US009566043B2

United States Patent
Kanade et al.

(10) Patent No.: US 9,566,043 B2
(45) Date of Patent: *Feb. 14, 2017

(54) SENSOR GUIDED CATHETER NAVIGATION SYSTEM

(71) Applicants: University of Pittsburgh—Of the Commonwealth System of Higher Education, Pittsburgh, PA (US); Carnegie Mellon University, Pittsburgh, PA (US)

(72) Inventors: Takeo Kanade, Pittsburgh, PA (US); David Schwartzman, Pittsburgh, PA (US); Hua Zhong, Pittsburgh, PA (US)

(73) Assignees: Carnegie Mellon University, Pittsburgh, PA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,048

(22) Filed: Apr. 20, 2015

(65) Prior Publication Data

US 2016/0256131 A1    Sep. 8, 2016

Related U.S. Application Data

(63) Continuation of application No. 13/915,974, filed on Jun. 12, 2013, now Pat. No. 9,017,260, which is a (Continued)

(51) Int. Cl.
*A61B 8/00*    (2006.01)
*A61B 5/05*    (2006.01)
(Continued)

(52) U.S. Cl.
CPC ............... *A61B 8/0841* (2013.01); *A61B 5/06* (2013.01); *A61B 5/065* (2013.01); *A61B 6/032* (2013.01);
(Continued)

(58) Field of Classification Search
CPC .......... A61B 5/06; A61B 5/065; A61B 6/541; A61B 8/12; A61B 8/4254; A61B 8/5238; A61B 8/543; G06T 2207/10016; G06T 2207/10081; G06T 2207/10136; G06T 2207/20076; G06T 2207/30021; G06T 2207/30048; G06T 7/0032
See application file for complete search history.

(56) References Cited

U.S. PATENT DOCUMENTS 5,379,223 A    1/1995    Asplund
5,592,939 A    1/1997    Martinelli
(Continued)

FOREIGN PATENT DOCUMENTS

WO    03/107275    12/2003
WO    2007/044792    4/2007

OTHER PUBLICATIONS

Title: Supplementary European Search Report Citation: EP 06825747.6 Publication Date: Jul. 26, 2013.
(Continued)

*Primary Examiner* — Michael Rozanski
(74) *Attorney, Agent, or Firm* — Dykema Gossett PLLC

(57) ABSTRACT

A method and a system for producing images of a subject, such as the heart of a human being. The method may comprise acquiring ultrasound images of the subject with a catheter comprising a position sensor. The method may also comprise capturing a plurality of 4D surface registration points in the acquired ultrasound images corresponding to points on the subject. The method may also comprise
(Continued)

registering, in space and time, a high-resolution 4D model of the subject with the plurality of 4D surface registration points. The method may also comprise displaying high resolution, real-time images of the subject during a medical procedure based on the registration of the high resolution 4D model to the 4D surface registration points. Embodiments of the present invention are especially useful in left atrium ablation procedures.

19 Claims, 9 Drawing Sheets

Related U.S. Application Data continuation of application No. 13/167,400, filed on Jun. 23, 2011, now Pat. No. 8,480,588, which is a continuation of application No. 12/083,044, filed as application No. PCT/US2006/039693 on Oct. 11, 2006, now Pat. No. 7,981,038.

(60) Provisional application No. 60/725,368, filed on Oct. 11, 2005.

(51) Int. Cl.
  *G06K 9/00* (2006.01)
  *A61B 8/08* (2006.01)
  *A61B 5/06* (2006.01)
  *A61B 8/12* (2006.01)
  *G06T 7/00* (2006.01)
  *A61B 6/03* (2006.01)
  *A61B 6/00* (2006.01)
  *A61B 5/0402* (2006.01)

(52) U.S. Cl.
  CPC .............. *A61B 6/5205* (2013.01); *A61B 8/12* (2013.01); *A61B 8/4254* (2013.01); *A61B 8/461* (2013.01); *A61B 8/5207* (2013.01); *A61B 8/5238* (2013.01); *G06T 7/0032* (2013.01); *A61B 5/0402* (2013.01); *A61B 6/541* (2013.01); *A61B 8/543* (2013.01); *G06T 2207/10016* (2013.01); *G06T 2207/10081* (2013.01); *G06T 2207/10136* (2013.01); *G06T 2207/20076* (2013.01); *G06T 2207/30021* (2013.01); *G06T 2207/30048* (2013.01)

(56) References Cited

U.S. PATENT DOCUMENTS

| | | | |
|---|---|---|---|
| 5,830,210 A | 11/1998 | Rudko | |
| 6,019,725 A | 2/2000 | Vesely | |
| 6,104,944 A | 8/2000 | Martinelli | |
| 6,216,026 B1 | 4/2001 | Kuhn | |
| 6,233,476 B1 | 5/2001 | Strommer | |
| 6,236,875 B1 | 5/2001 | Bucholz | |
| 6,246,898 B1 | 6/2001 | Vesely | |
| 6,317,621 B1 | 11/2001 | Graumann | |
| 6,368,285 B1 | 4/2002 | Osadchy | |
| 6,490,467 B1 | 12/2002 | Bucholz | |
| 6,493,573 B1 | 12/2002 | Martinelli | |
| 6,556,695 B1 | 4/2003 | Packer | |
| 6,623,431 B1 | 9/2003 | Sakuma | |
| 6,663,625 B1 | 12/2003 | Ormsby | |
| 6,774,624 B2 | 8/2004 | Anderson | |
| 6,783,536 B2 | 8/2004 | Vilsmeier | |
| 6,892,090 B2 | 5/2005 | Verard | |
| 6,895,267 B2 | 5/2005 | Panescu | |
| 6,920,347 B2 | 7/2005 | Simon | |
| 6,947,786 B2 | 9/2005 | Simon | |
| 6,968,224 B2 | 11/2005 | Kessman | |
| 6,990,368 B2 | 1/2006 | Simon | |
| 7,007,699 B2 | 3/2006 | Martinelli | |
| 7,015,859 B2 | 3/2006 | Anderson | |
| 7,089,063 B2 | 8/2006 | Lesh | |
| 7,103,399 B2 | 9/2006 | Miga | |
| 7,139,601 B2 | 11/2006 | Bucholz | |
| 7,211,082 B2 | 5/2007 | Hall | |
| 7,343,195 B2 | 3/2008 | Strommer | |
| 7,604,601 B2 | 10/2009 | Altmann | |
| 7,981,038 B2 | 7/2011 | Kanade | |
| 8,480,588 B2* | 7/2013 | Kanade | A61B 5/06 382/128 |
| 9,017,260 B2* | 4/2015 | Kanade | A61B 5/06 382/128 |
| 2001/0031919 A1 | 10/2001 | Strommer | |
| 2001/0047133 A1 | 11/2001 | Gilboa | |
| 2002/0042571 A1 | 4/2002 | Gilboa | |
| 2002/0049375 A1 | 4/2002 | Strommer | |
| 2002/0193686 A1 | 12/2002 | Gilboa | |
| 2003/0114778 A1 | 6/2003 | Vilsmeier | |
| 2003/0160721 A1 | 8/2003 | Gilboa | |
| 2003/0216639 A1 | 11/2003 | Gilboa | |
| 2004/0030244 A1 | 2/2004 | Garibaldi | |
| 2004/0087996 A1 | 5/2004 | Gambale | |
| 2004/0097805 A1 | 5/2004 | Verard | |
| 2004/0097806 A1 | 5/2004 | Hunter | |
| 2004/0147837 A1 | 7/2004 | Macaulay | |
| 2004/0242995 A1 | 12/2004 | Maschke | |
| 2004/0249267 A1 | 12/2004 | Gilboa | |
| 2005/0049510 A1 | 3/2005 | Haldeman | |
| 2005/0137661 A1 | 6/2005 | Sra | |
| 2005/0148853 A1 | 7/2005 | Redel | |
| 2005/0148859 A1 | 7/2005 | Miga | |
| 2005/0182319 A1 | 8/2005 | Glossop | |
| 2005/0203394 A1 | 9/2005 | Hauck | |
| 2005/0288577 A1 | 12/2005 | Weese | |
| 2006/0009755 A1 | 1/2006 | Sra | |
| 2006/0116575 A1 | 6/2006 | Willis | |
| 2006/0116576 A1 | 6/2006 | McGee | |
| 2006/0144407 A1 | 7/2006 | Aliberto | |
| 2006/0173287 A1 | 8/2006 | Sabczynski | |
| 2006/0184016 A1 | 8/2006 | Glossop | |
| 2006/0247522 A1 | 11/2006 | McGee | |
| 2007/0016005 A1 | 1/2007 | Timinger | |
| 2007/0021744 A1 | 1/2007 | Creighton | |
| 2007/0055141 A1 | 3/2007 | Kruger | |
| 2007/0073288 A1 | 3/2007 | Hall | |
| 2007/0135713 A1 | 6/2007 | Borgert et al. | |
| 2007/0167738 A1 | 7/2007 | Timinger | |
| 2007/0179496 A1 | 8/2007 | Swoyer | |
| 2007/0197905 A1 | 8/2007 | Timinger | |
| 2007/0232898 A1 | 10/2007 | Huynh | |
| 2007/0276216 A1 | 11/2007 | Beyar | |
| 2007/0287909 A1 | 12/2007 | Garibaldi | |
| 2007/0293721 A1 | 12/2007 | Gilboa | |
| 2008/0006280 A1 | 1/2008 | Aliberto | |
| 2008/0015670 A1 | 1/2008 | Pappone | |
| 2008/0021297 A1 | 1/2008 | Boosten | |
| 2008/0051721 A1 | 2/2008 | Carter | |
| 2008/0119785 A1 | 5/2008 | Ramsey | |

OTHER PUBLICATIONS

Zhong, Hua, "Sensor Guided Ablation Procedure of Left Atrial Endocardium"; Medical Image Computing and Computer-Assisted Intervention (MICCAI), Lecture Notes in Computer Science (LNCS) 3750 Reference pp. 1-8 Publication Date: Oct. 26, 2005.
Zhong, Hua; "Virtual Touch: An Efficient Registration Method for Catheter Navigation in Left Atrium"; Medical Image Computing and Computer-Assisted Intervention (MICCAI), Lecture Notes in Computer Science (LNCS) 4190; Reference pp. 437-444; Publication Date: Oct. 1, 2006.
International Search Report in PCT Application No. PCT/US2006/039693 (Feb. 22, 2007).

* cited by examiner

CT Scan

Segmented CT

Model t = 0.0

Model t = 0.5

Before Time Alignment

After Time Alignment

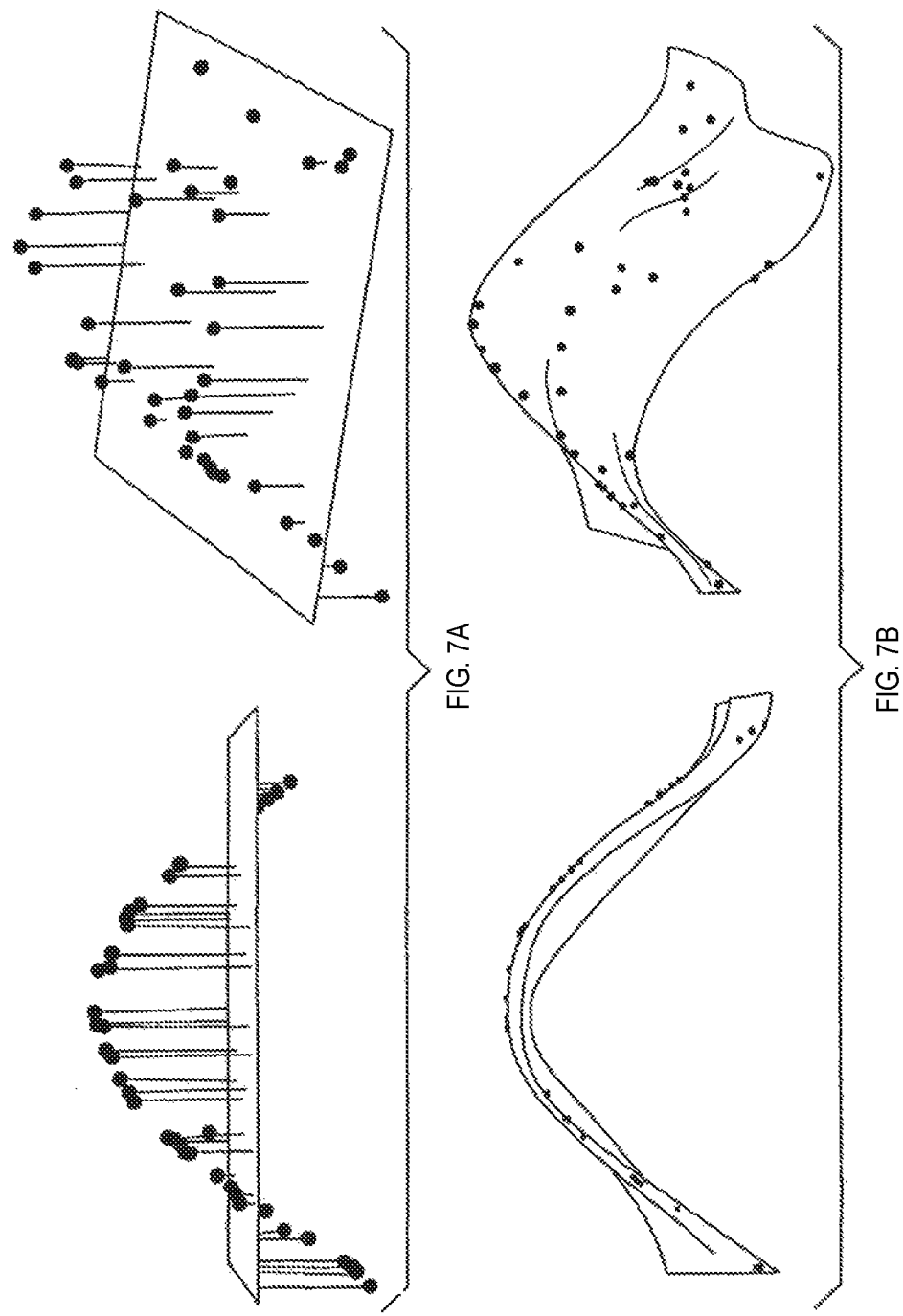

SENSOR GUIDED CATHETER NAVIGATION SYSTEM

CROSS-REFERENCE TO RELATED APPLICATIONS

This application is a continuation of U.S. application Ser. No. 13/915,974, filed 12 Jun. 2013 (the '974 application), now U.S. Pat. No. 9,017,260, which is a continuation of U.S. application Ser. No. 13/167,400, filed 23 Jun. 2011 (the '400 application), now U.S. Pat. No. 8,480,588, which is a continuation of U.S. application Ser. No. 12/083,044, filed 23 Oct. 2008 (the '044 application), now U.S. Pat. No. 7,981,038, which is a national stage of international application no. PCT/US2006/039693, filed 11 Oct. 2006 (the '693 application), now expired, which claims the benefit of priority to U.S. application No. 60/725,368, filed 11 Oct. 2005 (the '368 application). The '974 application, '400 application, '044 application, '693 application and the '368 application are each hereby incorporated by reference as though fully set forth herein.

BACKGROUND OF THE INVENTION a. Field of the Invention

The present invention relates generally to catheters and catheter navigation systems.

b. Background Art

Recent years have witnessed an expanding need for percutaneous, endocardium-based cardiac interventions, including ablation, injection, and device deployment. These interventions are generally not focal, but rather involve a broad region of endocardial anatomy. This anatomy is complex topographically, as well as motile. Current modalities for real-time intraoperative endocardial imagining and navigation are highly inaccurate, which has been the cause of procedure inefficiency and complications.

One such procedure is catheter ablation of the left atrial endocardium. This procedure is performed in an attempt to cure atrial fibrillation, a common heart rhythm disorder. The left atrium, as noted above, has a complex topography and motility. At present, the ablation procedure is performed by attempting to "register" preoperative four-dimensional imaging data (derived from computed tomography) and with two-dimensional intraoperative imaging data derived from intracardiac echocardiography and fluoroscopy). This is laborious, highly operator-dependent (which prohibits dissemination) and inaccurate.

Typically, two major sensor systems are used during ablation procedures to assist clinicians to navigate catheters: (1) a magnetic tracking system, which can track the 3D position of the catheter tip and yaw, pitch, and roll of the catheter; and (2) intracardiac ultrasound imaging sensor, which can generate a 2D section view in real time inside the heart chambers. Sometimes X-ray pictures are used as well. Apparently, all these sensors are used independently. That is, an ultrasound-imaging sensor is used to see visually if the ablation catheter is touching the hard wall and the magnetic tracking system is used to visualize the ablation sites without any relative position information to the heart.

In order to visualize the catheter's position relative to the heart, the registration must be done between the magnetic tracking system and a heart model derived from a CT scan or an MRI captured prior to surgery. Some similar 3D registration systems are available for surgery of rigid body parts, such as hipbone surgery. Software such as BioSense Webster's CARTOMERGE can be used to do the 3D registration between the magnetic tracking system and the 3D heart model from the CT scan. These systems basically do the registration based on 3D shape. In order to do the registration, a set of registration points needs to be captured. That is, clinicians need to move a probe or catheter whose position is tracked to touch the surface of the bones or heart wall and record all those positions.

These systems work well with rigid or almost rigid human body parts, such as bones or brain. In contrast, the shape of the human heart changes dramatically through every cardiac cycle. Also, the respiration or breath of a person can also change the pressure of the person's lung and eventually change the shape of the person's heart.

Relevant prior art includes U.S. Pat. No. 6,556,695, which discloses a method and system for high resolution medical images in real-time to assist physicians in the performance of medical procedures. The disclosed method includes: acquiring image data of the subject anatomy and reconstructing an image which is a high resolution model of the subject anatomy; performing a medical procedure in which the subject anatomy is imaged in real-time by acquiring low resolution images at a high frame rate; registering the high resolution model of the subject anatomy with each acquired low resolution image; and displaying to the physician in real-time images of the registered high resolution model of the anatomy. The high-resolution model may be a 2D or 3D image of static anatomy, or it may be a 4D model in which the fourth dimension depicts changes in the anatomy as a function of time, cardiac phase, respiratory phase, or the like. The creation of this model is performed using a high resolution imaging modality and it may be done prior to performing the medical procedure. The registration of the high resolution model is performed in real-time and includes a 2D or 3D spatial orientation as well as a registration in time or phase when the model depicts changing anatomy.

BRIEF SUMMARY OF THE INVENTION

In one general aspect, the present invention is directed to a method for producing images of a subject, such as the heart of a human being. According to various embodiments, the method comprises acquiring ultrasound images of the subject (e.g., the inner walls of the subject's heart) with a catheter that comprises a position sensor. The method also comprises capturing a plurality of 4D surface registration points in the acquired ultrasound images corresponding to points on the subject (e.g., points on the inner walls of the subject's heart). The method also comprises registering, in space and time, a high-resolution 4D model of the subject (e.g., a 4D-heart model) with the plurality of 4D surface registration points. The method may also comprise displaying high resolution, real-time images of the subject during a medical procedure based on the registration of the high resolution 4D model to the 4D surface registration points. In that way, as the clinician (e.g., surgeon) moves the catheter as part of a medical procedure, the clinician may be presented with real-time, high resolution 3D images of the subject (rather than ultrasound images), which may aid the clinician in the procedure. Also, unlike the prior art where the clinician has to actually touch the catheter to the subject to collect the registration points, the registration points can be captured with a "virtual touch" with the present invention by which tens of thousands of high quality surface points can be captured within a few minutes without physically touching the catheter to the subject. Embodiments of the present invention are especially useful in left atrium ablation procedures, which is a procedure sometimes used in an attempt to cure atrial fibrillation, although it should be recognized that the present invention could be used for other types of procedures and for different parts/organs of the human body.

According to various implementations, the registration of the high resolution 4D model of the subject with the plurality of 4D surface registration points may be based on data regarding the position of the catheter and a timing signal (e.g., an ECG signal). Also, the high resolution 4D model may be generated from a series of 3D models at successive time points, such CT scans at different points of a cardiac cycle. The registration process may involve iteratively determining a transformation function that aligns the 4D surface registration points to the 4D model so that the 4D surface registration points are on the 4D model (e.g., in the inner heart walls). The registration process may further involve refining the registration based on a free-form non-rigid registration.

In another general aspect, the present invention is directed to a catheter navigation system. According to various embodiments, the catheter navigation system may comprise a catheter that comprises an ultrasound transducer and a magnetic position sensor. The system also comprises a position tracking system for tracking the position of the catheter based on signals received by the magnetic position sensor. In addition, the system comprises an image processing module in communication with the catheter and the position tracking system for: (i) capturing a plurality of 4D surface registration points from a plurality of ultrasound images of a subject acquired by the catheter; and (ii) registering, in time and space, a high resolution 4D model of the subject with the plurality of 4D surface registration points.

In various implementations, the system may also comprise a display for displaying high resolution, real-time images of the subject during a medical procedure based on the registration of the high resolution 4D model to the 4D surface registration points. Additionally, the image-processing module may register the high-resolution 4D model of the subject with the plurality of 4D surface registration points by iteratively determining a transformation function that aligns the 4D surface registration points to the 4D model so that 4D surface registration points are on the 4D model. Also, the image-processing module may refine the registration based on a free-form non-rigid registration. In addition, the high resolution 4D model may be based on 3D CT scans of the subject generated at successive time points (such as various points of a cardiac cycle).

In another general aspect, the present invention is directed to a computer readable medium having stored thereon instructions, which when executed by a processor, cause the processor to: (1) capture a plurality of 4D surface registration points from a plurality of input ultrasound images corresponding to points on a subject (e.g., inner walls of the subject's heart); and (2) register, in space and time, a high resolution 4D model of the subject with the plurality of surface registration points. The computer readable medium may also include instructions which when executed by the processor cause the processor to display the high resolution, real-time images of the subject during a medical procedure on the subject based on the registration of the high resolution 4D model to the 4D surface registration points.

In yet another general aspect, the present invention is directed to a method of performing a medical procedure on a subject. According to various embodiments, the method comprises inserting, by a clinician (e.g., a surgeon), a first catheter into the subject (such as the heart of the subject), wherein the first catheter comprises an ultrasonic transducer.

The method also comprises acquiring ultrasound images of the subject with the first catheter and capturing, with a programmed computer device in communication with the catheter, a plurality of 4D surface registration points in the acquired ultrasound images corresponding to points on the a portion of the subject (e.g., the inner heart walls of the subject). The method may further comprise registering, with the programmed computer device, a high-resolution 4D model of the subject with the plurality of surface registration points. The method may also comprise displaying, on a display in communication with the computing device, high resolution, real-time images of the subject during the medical procedure based on the registration of the high resolution 4D model to the 4D surface registration points.

In various implementations, the first catheter further comprises an interventional device, and the method may further comprise the steps of: (1) navigating, by the clinician, the position of the first catheter based on the displayed high resolution images; and (2) performing, by the clinician, a procedure using the interventional device on the subject.

In another general implementation, the method may comprise inserting a second catheter into the subject, wherein the second catheter comprises an interventional device. The method may further comprise the steps of: (1) navigating, by the clinician, the position of the second catheter based on the displayed high-resolution images; and (2) performing, by the clinician, a procedure on the subject with the interventional device of the second catheter.

BRIEF DESCRIPTION OF THE DRAWINGS

Various embodiments of the present invention are described herein by way of example in conjunction with the following figures wherein:

FIGS. 7A and 7B illustrate an example of non-rigid local registration;

DETAILED DESCRIPTION OF THE INVENTION

Figure 1:
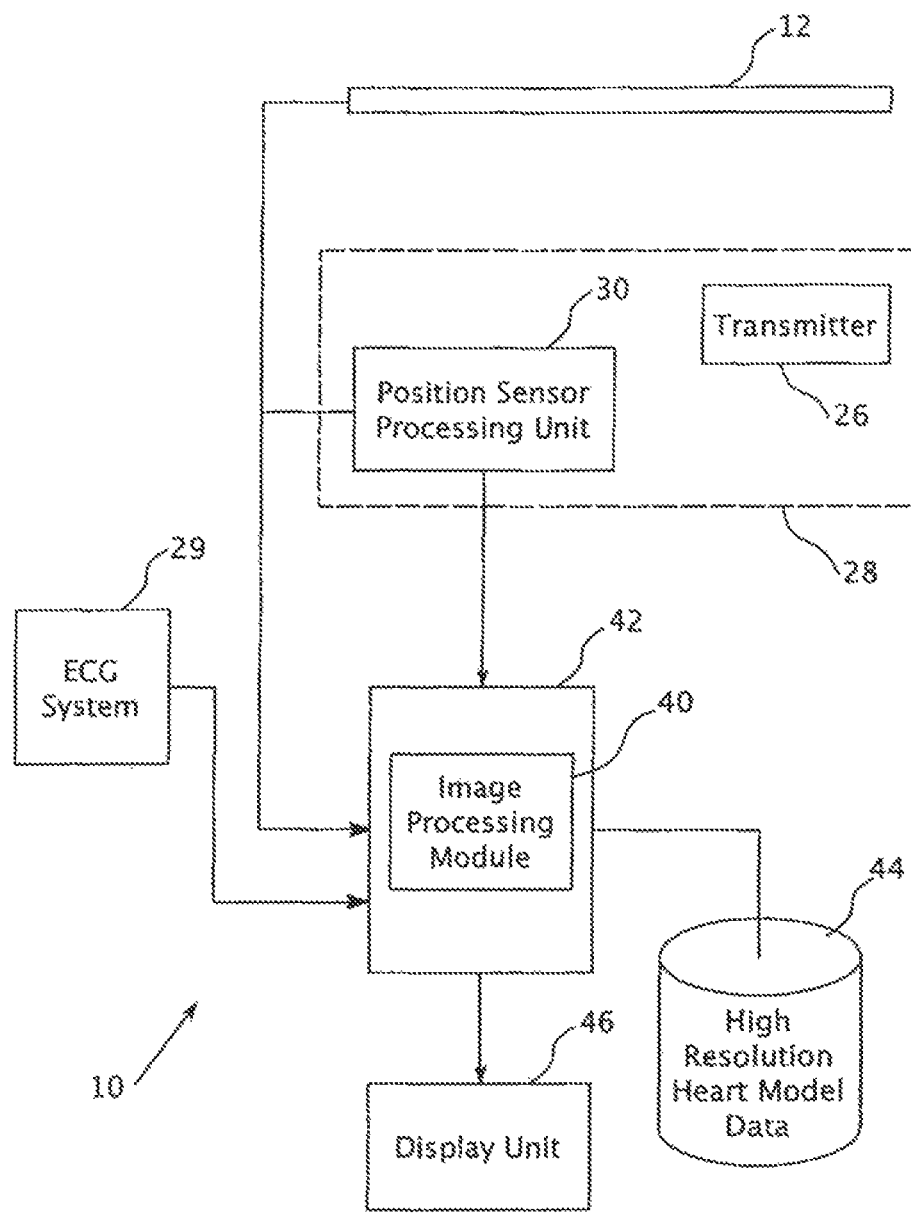
FIG. 1 is a diagram of a catheter navigation system according to various embodiments of the present invention.

FIG. 1 is a simplified diagram of a catheter navigation system 10 according to various embodiments of the present invention. As shown in FIG. 1, the catheter navigation system may comprise a catheter 12, which may be inserted into the body of a subject (not shown). The catheter navigation system 10 generates high resolution, 3D, real-time images of the environment of the catheter 12. The catheter navigation system 10 is especially useful in producing high resolution, 3D, real-time images of non-rigid and/or topographically complex bodies, such as, for example, the human heart. In particular, the catheter navigation system 10 is especially useful for procedures involving the left atrium such as left atrium ablation.

Figure 2:
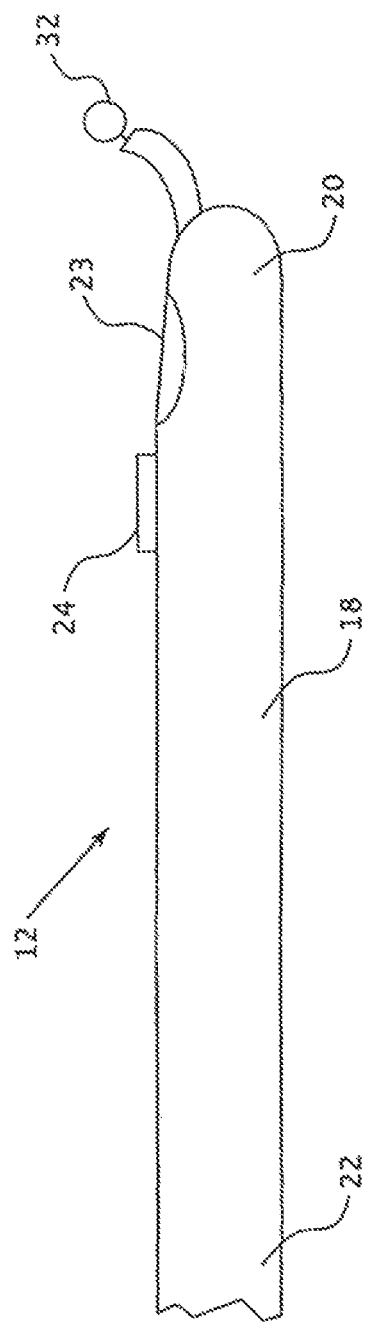
FIG. 2 is a diagram of the distal end of a catheter for use in the catheter navigation system of FIG. 1 according to various embodiments of the present invention.

As shown in FIG. 2, the catheter 12, according to various embodiments, may include an elongated flexible or rigid plastic tubular body 18 having a distal end 20 and a proximal end 22. At the distal end 20, the catheter 10 may include an ultrasound transducer 23 for transmitting ultrasound and for receiving resultant echoes from surrounding objects (such as the inner walls of a heart when the catheter 12 is positioned inside the heart) so as to provide a field of view for the distal end 20 of the catheter 12.

The catheter 10 may also include a magnetic position sensor 24, which may comprise a number of coils (not shown) for detecting signals emitted from a transmitter 26 of a position tracking system 28 (see FIG. 1). For example, the magnetic position sensor 24 may comprise three mutually orthogonal coils. The transmitter 26 may also include, for example, three mutually orthogonal emitting coils. The sensor 24 may detect magnetic fields produced by the transmitter 26 and the output of the sensor 24 may be input to a position tracking processing unit 30 (see FIG. 1) of the position tracking system 28. Based on the signals received by the sensor 24, the position tracking processing unit 28 may compute the position and orientation (roll, pitch, and yaw) of the sensor 24 (and hence the position and orientation of the distal end 22 of the catheter 10). The processing unit 28 may comprise, for example, a PCB with a processor and firmware for computing the position of the position 24 based on the received signals. The processing unit 28 may also input control signals to a drive control unit (not shown) for the transmitter 26 to activate selectively the desired output from the transmitter 26. According to various embodiments, the microBIRD position tracking system from Ascension Technologies could be used for the position tracking system 28. For more details, see published U.S. patent application Pub. No. 2004/0088136 A1, incorporated herein by reference.

Using a catheter 12 with both an ultrasound transducer 23 and a position sensor 24 as described above not only allows the 3D coordinates, yaw, pitch, and roll of the catheter's tip (i.e., the distal end 20) to be determined, but also the 3D coordinates of every pixel in the ultrasound image as described below, thereby obviating the need to physically touch the subject's heart with the catheter to record registration points, as is required in the prior art.

In various embodiments, the catheter 12 may also include an interventional device, such as, for example, an ablation device, a drug/cell delivery device, a suture device, a pacing device, an occlusion/excision instrument, etc. In FIG. 2, the catheter 10 is shown as having an ablation device 32 for ablating an area of the subject, such as the inner walls of the subject's heart. Left atrium ablation is a procedure that attempts to cure atrial fibrillation. During the surgery, an ablation catheter is inserted into the left atrium through the vein. Clinicians need to navigate the ablation catheter to ablate the areas where the left and right pulmonary veins meet the left atrium. With the ultrasound transducer 23 and the ablation device 32 on one catheter 10, the clinician may only need to insert one catheter into the subject's heart to both (1) acquire the images of the heart and (2) perform the ablation.

According to other embodiments, two or more catheters could be used. In such embodiments, the clinician could insert a second catheter (the ablation catheter) into the relevant area of the heart where the second catheter includes the ablation device. Preferably, such an ablation catheter would also include a position sensor so that the position tracking system 28 could track the position and orientation of the second catheter. That way, the clinician could use one catheter for acquiring the ultrasound images and the other catheter to perform the ablation.

Referring back to FIG. 1, the received ultrasound images picked up by the ultrasound transducer 23 are input to an image processing module 40 of a computer device 42. The catheter 12 may be in communication with the computing device 42 using any suitable type of communication interface, such as a wired interface (e.g., RS-232 or USB) or a wireless interface.

The image processing module 40, as described in more detail below, may generate high resolution, real-time 3D images of the object being scanned by the catheter 10 (such as the inner walls of the subject's heart) based on (i) the ultrasound images picked up by the ultrasound transducer 23, (ii) data regarding the position of the catheter 10 from the position tracking system 28, (iii) previously acquired high resolution image data of the object (e.g., the subject's heart), which may be stored in a memory unit 44, and (iv) timing signals (e.g., electrocardiogram (ECG) signals from a ECG system 29). As described in more detail below, the image-processing module 40 may first perform a time-space registration between a 4D model of the subject area (e.g., the subject's heart) and surface registration points on the ultrasound images from the catheter 12. Once the registration is complete, the image processing module 40 may generate and output real-time, high resolution 3D models of the subject (e.g., the subject's heart) on a display unit 46, which can be viewed by a clinician (e.g., a surgeon) as the clinician moves the catheter 12 as part of a medical procedure (e.g., a left atrium ablation). The real-time images may be based on real-time ultrasound image data being captured by the catheter 12 as part of the procedure, the position of the catheter 12 (as determined by the position tracking system 28), and on the timing signals (e.g., the ECG signals).

The ECG system 29 may measure the electrical activity of the subject's heart as is known in the art. As described in more detail below, the ECG signals from the subject may be used to synchronize the ultrasound image data captured by the catheter 12 with the 4D heart model.

The computer device 42 may be implemented as any type of computer device suitable for the application. For example, the computer device 42 may be a personal computer, a workstation, etc. The image-processing module 40 may be implemented as software code to be executed by a processor (not shown) of the computer device 40 using any suitable computer language using, for example, conventional or object-oriented techniques. The software code may be stored as a series of instructions or commands on a computer-readable medium, such as a random access memory (RAM), a read-only memory (ROM), a magnetic medium such as a hard drive or a floppy disk, or an optical medium, such as a CD-ROM. The memory unit 44 storing the previously acquired high-resolution image data of the object may also be a random access memory (RAM), a read-only memory (ROM), a magnetic medium such as a hard drive or a floppy disk, or an optical medium, such as a CD-ROM. The display unit 46 may be any suitable type of monitor, such as a LCD display, for example. In addition, according to various embodiments, the position-tracking unit 30 could be implemented as a module of the computer device 42.

Figure 3:
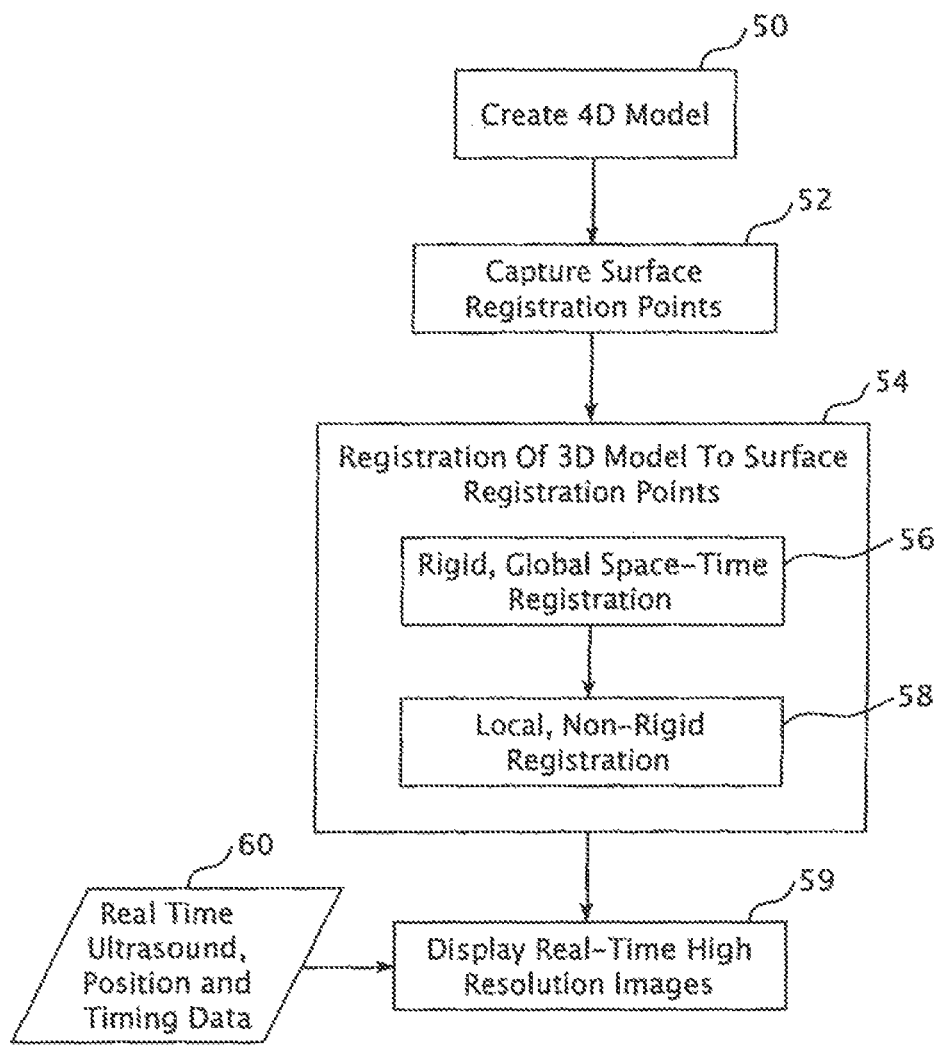
FIG. 3 is a flow chart of the process flow of the image-processing module of the catheter navigation system of FIG. 1 according to various embodiments of the present invention.
Figure 4A:
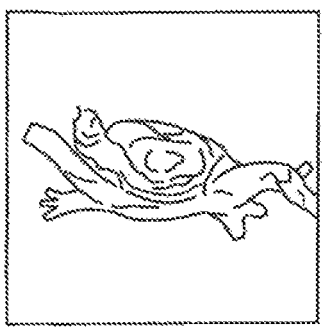
FIG. 4A shows a CT scan of a human heart.
Figure 4B:
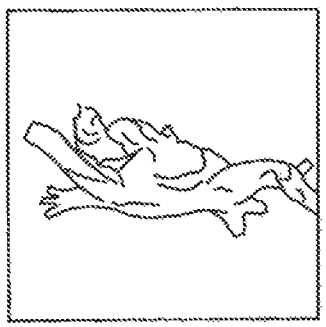
FIG. 4B shows a segmented CT scan.
Figure 4C:
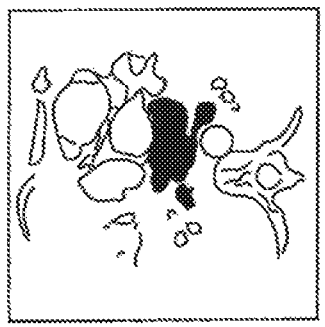
FIGS. 4C and 4D show models of the heart at different times in the cardiac cycle.
Figure 4D:
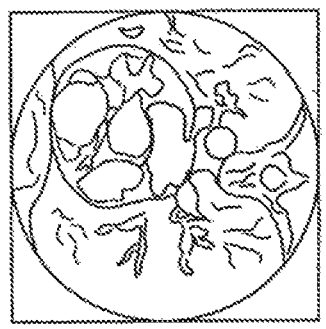

FIG. 3 is a diagram of the process flow of the image-processing module 40 according to various embodiments of the present embodiment. In the following description, it is presumed that the catheter 10 is inserted into a human heart and is that the image-processing module 40 is for generating high resolution, real time, 3D images of the heart, although it should be recognized that the catheter navigation system could be used for other purposes.

At step 50, the image processing module 40 creates a 4D model of the subject's heart based on previously-acquired high resolution image data of the subject's heart, which may be stored in memory unit 44. The previously acquired high-resolution image data may be acquired by any suitable means, including, for example, computer tomography (CT) scans or magnetic resonance imaging (MRI). The high-resolution image data is preferably acquired before the catheterization such as, for example, one day before under the assumption that the heart shape will not change in such a short period of time. The high-resolution image data may depict the subject's heart in three spatial dimensions at successive points (or phases) of the cardiac cycle. Thus, time is the fourth dimension. According to various embodiments, a CT scanner that generates a 3D heart scan at every 10% of a cardiac cycle may be used, so that in total there may be ten 3D CT scans for one cardiac cycle. Such a CT scanner is available from General Electric.

Figure 10:
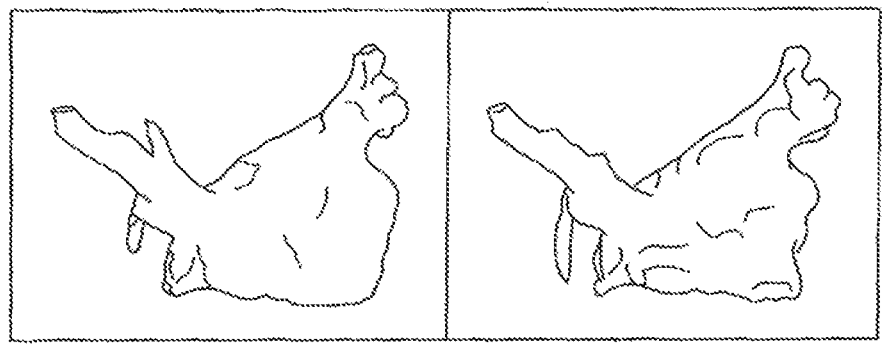
FIG. 10 shows an example of a 4D heart model.

To construct the 4D model, data for the left atrium may be segmented out manually. Then the image-processing module 40 may extract the surface model from the segmented CT data using, for example, the Marching Cube (MC) algorithm. The density threshold of MC algorithm may be set to represent the surface between blood and heart muscle. Small floating parts may be removed by discarding all triangles except those in the largest connecting group of the model. Post processing may be performed to smooth the model and reduce artifacts based on geometry cues with an implicit integration method. For more details, see Mathieu Desbrun et al., "Implicit fairing of irregular meshes using diffusion and curvature flow", Computer Graphics, 33 (Annual Conference Series):317-324, 1999, which is incorporated herein by reference. For ten CT scans, ten surface models can be extracted across one cardiac cycle, with each model corresponding to the shape of the left atrium at one time (or phase) within the cardiac cycle. This is the 4D heart shape model. The example of FIG. 10 shows two 3D heart models as different points in the cardiac cycle. Because the heart is beating, the shape changes through the cycle.

Next, at step 52, 4D surface registration points on the inner walls of the subject's heart are captured based on the ultrasound images captured by the catheter 12. In the past, the clinician had to touch physically the catheter to the wall of the heart to capture each surface point. In contrast, with embodiments of the present invention, the catheter 12 can capture tens of thousands of high quality surface points within a few minutes without physically touching the heart wall. The inventors refer to this technique as "virtual touch." "Virtual touch" can scan a rough 4D heart shape (thousands of wall points) during the operation. This heart shape may not have the high resolution of a CT scan but it is what the heart is like during the operation. Such rough shape has much more information than just a few points on the heart wall and it may greatly improve the accuracy and stability of registration.

Figure 8:
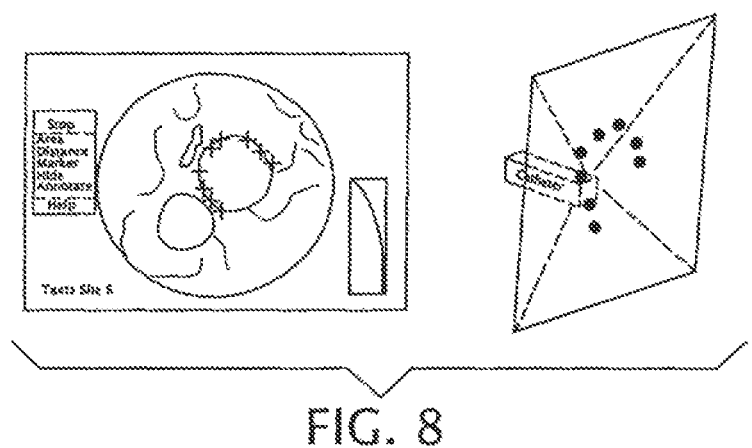
FIGS. 8 and 9 illustrate the concept of "virtual touch," whereby, according to various embodiments of the present invention, clinicians can take numerous ultrasound images of an object (e.g., a heart) to capture 4D surface registration points for the object.
Figure 9:
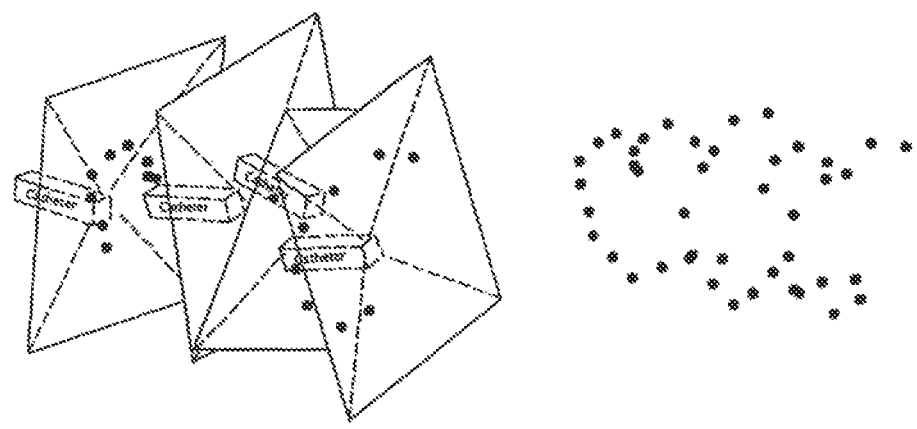

With a catheter having a position sensor 24, when the clinician moves the catheter 12 to a certain location and takes an ultrasound image of the heart, the clinician can see those pixels that are on the heart wall, as shown in the examples of FIGS. 8 and 9. Usually these pixels have high gradient values and they can be detected by image processing algorithms such as edge detectors. Not all of the pixels that are on the heart wall need to be detected, but rather only the ones with the highest confidence levels. Using a catheter 12 with a position sensor 24 allows not only the tip, but also every ultrasound image pixel's 3D coordinates to be computed based on information from the magnetic position tracking system 28. Thus, detecting those pixels that are on the wall is equivalent to having physically moved the catheter to that location, touched the heart wall and recorded the catheter tip's 3D coordinates. For one ultrasound image, it is not difficult to touch virtually hundreds of points that are on the heart wall. Moreover, the clinician can move the catheter 12 inside the heart and take ultrasound images moving the catheter.

The locations and times of those ultrasound images are also recorded. For each image, one virtually touches the heart wall. The registration points from one ultrasound image may have the same time coordinate as when the image is taken. The time coordinate may be between 0 and 1, where 0 means at the beginning of a cardiac cycle and 1 designates the end of a cardiac cycle. Intuitively, more registration points usually generate a better registration result. By using a catheter with a position sensor, one can record real time ultrasound video while moving the catheter and, as a result, hundreds or thousands of registration points can be captured.

Each 3D surface model extracted from the CT data may therefore correspond to a time $t \in [0, 1]$ (suppose t=0 is at the beginning of a cardiac cycle and t=1 is at the end of a cardiac cycle) in a cardiac cycle when the heart was CT scanned. In the description to follow, $C=\{C_0, C_1, \ldots, C_{n-1}\}$ is used to represent the 4D heart model, where n is the number of 3D models for one cardiac cycle. For example, n may equal ten, corresponding to one 3D CT scan at every 10% of a cardiac cycle, so ten surface models may be extracted, corresponding to $C=\{C_0, C_1, \ldots, C_9\}$, where each model $C_i$ represents the heart shape at time t=i/10, i=0, 1, . . . , 9. An example of this process is shown in FIGS. 4A-4D.

Figure 11:
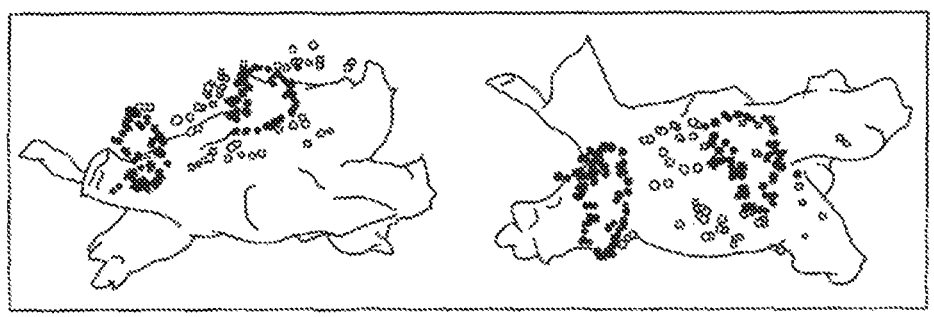
FIG. 11 shows an example of space registration.

Referring back to FIG. 3, at step 54, the image processing module 15 may register the 4D heart model to the 4D surface registration points. Both the 4D heart model and the 4D surface registration points may be synchronized with ECG signals (from the ECG system 29) as the time coordinates. As shown in FIG. 3, the registration step may comprise two processes: first, at step 56, a rigid, global space-time registration between the 4D heart model and the 4D surface registration points; and second, at step 58, a local non-rigid registration to further improve the registration accuracy. As explained below, the first process may comprise, tentatively finding a transformation function F that can align the 4D surface registration points to the 4D heart model so that most or all the 4D surface registration points are on the inner heart wall of the model, as shown in the example of FIG. 11. FIG. 11 shows an example of registration points and a heart model before and after registration. As can be seen in the right-hand side image in FIG. 11, after registration the surface points are on the heart walls of the model. The time axis is also preferably aligned. The local non-rigid registration (step 56) may employ a free-form non-rigid registration.

For the global, rigid time-space registration, an initial space registration can be done in a coarse-to-fine scheme. First, a rough alignment can be found based on the orientation of the subject on the bed. This rough alignment can be further refined by some points captured on some designated regions of the heart. These regions should be easy to locate solely from ultrasound images, such as the entrance region of pulmonary veins. Then an alignment can be found so that these points are near the same regions in the heart model as where they were captured.

Figure 5A:
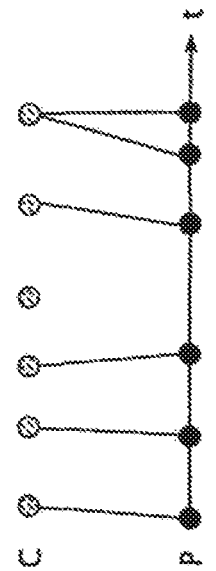
FIGS. 5A and 5B shows an example of time alignment between a model and sets of registration points.
Figure 5B:
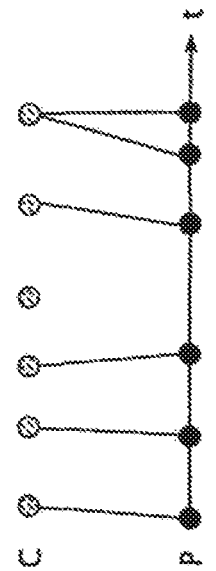

Time registration may be equal to a correspondence scheme S that indicates for any point set $P_i$ in P, which $C_j$ in C is its correspondence according to time. The heart model $C=\{C_0, C_1, \ldots, C_9\}$ and the 4D surface registration points $P=\{P_0, P_1, \ldots, P_9\}$ were preferably captured both at t=0, 0.1, . . . , 0.9. Ideally, the time registration should be $P_i$ corresponds to $C_i$ for any i. Preferably, both the heart model and the surface registration points are synchronized to the ECG signal to determine the time coordinate. Under different conditions, sometimes the patient's heart beat rate is not stable, in which case the one-on-one correspondence of $C_i$ with $P_i$ may not be true. So time alignment may be necessary, as shown in FIGS. 5A and 5B. In these figures, the upper row represents models and lower row represents point sets. The x-axis represents time. In the initial time alignment, shown in FIG. 5A, a one-on-one correspondence may be assumed. The best correspondence scheme, shown in FIG. 5B, will be found after time alignment. For initial time registration, the correspondence scheme of $P_i$ to $C_i$ for any $i \in [0; 9]$ may be used.

The 4D registration algorithm employed by the image-processing module 40 may assume errors have a Gaussian distribution. In that case, the registration algorithm needs to find a space transformation function F and a time correspondence scheme S that maximizes the expectation of log likelihood of p(F(P)|S, C). The probability p(F(P)|S, C) can be defined as:

$$p(F(P)|S, C) = \prod_i p(F(P_i)|C_{si}) \quad (1)$$
$$= \prod_i (\exp(-\|F(P_i), C_{si}\|))$$

Here $C_{si}$ is the corresponding model for $P_i$ defined by scheme S. Each $p(F(P_i)|C_{si})$ can be defined as an exponential function of the average distance from every point in $F(P_i)$ to model $C_{si}$, which is written as $\|F(P_i), C_{si}\|$.

The number of n (number of CT scans within a cardiac cycle) and m (number of time spots the magnetic tracking system can record point coordinates) can be adjusted so that n=m×d, where d is an integer. According to various embodiments, the t coordinates of the magnetic tracked points and the surface models from the CT scans can be assumed to be perfectly synchronized. Then any magnetic tracked point in point set $P_i$ should have the same t coordinate as heart model $C_{ixd}$. If the t in the CT scans and magnetic tracking system are not perfectly synchronized, a definite one-on-one correspondence may not exist. If $P_i$ is assumed to be independent of all other $C_j$ except the corresponding one $C_{ixd}$, then $$p(F(P)|C) = p(F(P_1)|C_1) \cdot p(F(P_2)|C_{2xd}) \cdot \ldots \cdot p(F(P_m)|C_n) \quad (2)$$

where n=m×d.

The probability of $p(F(P_i)|C_j)$ can de defined as the exponential function of the average square distance from each point in $F(P_i)$ to the surface model $C_j$:

$$p(F(P_i)|C_j) = \exp\left(\frac{-\sum_{p_k \in P_i} \|p_k - C_j\|^2}{|P_i|}\right) \quad (3)$$

The distance from a point to a model $\|P_k - C_j\|$ may be defined as the distance from point $P_k \in P_i$ to its nearest point in the surface model $C_j$. $|P_i|$ is the number of points in $P_i$.

To maximize the probability in equation (2), a modified ICP (Iterative Closest Point) algorithm may be used. For more details, see P. J. Besl et al., "A method for registration of 3-d shapes," IEEE Trans. Pattern Analysis and Machine Intelligence, pages 14:239-256, 1992, which is incorporated herein by reference. The ICP algorithm iteratively minimizes the distance between a set of points P and model C. In a standard ICP algorithm, each iteration contains two steps:

Compute the nearest point in Model C for each point in point set P.

Find a transformation F that can minimize the distance from P to their nearest points, and then replace P with F(P) and repeat. According to embodiments of the present invention, during the first step, for each point set $P_i$, the nearest point set $P_{near\_i}$ can be found only from model $C_{ixd}$. In order to maximize the whole p(F(P)|C) other than any single term of $p(F(P_i)|C_j)$, in the second step, all the point sets may be combined together as well as their nearest point sets, $P_{combine} = U_{i=1}^{m} P_i$ and $P_{near\_combine} = U_{i=1}^{m} P_{near\_i}$, and a transformation F may be found like in standard ICP for this combined point set $P_{combine}$ and $P_{combine\_near}$. In this way, a transformation function F that maximizes the probability p(F(P)|C) can be found. The modified ICP can be summarized as:

Compute the nearest point set $P_{near\_i}$ for each $P_i$ in their corresponding model $C_{ixd}$.

Combine point sets $P_{combine} = U_{i-1}^{m} P_i$ and $P_{near\_combine} = U_{i-1}^{m} P_{near\_i}$, and find a transformation function F that minimizes the distance from $F(P_{combine})$ to $P_{near\_combine}$, then replace the original $P_i$ with $F(P_i)$ and repeat. There are many ways to accelerate ICP and make it more robust. Any or all those algorithms can be applied according to various embodiments of the present invention. For example, a K-D tree acceleration may be used for the nearest neighbor search, and to ensure convergence to a global minimum, a random perturbation may be added to the found results and the ICP algorithm may be re-run.

During a heart operation, the t coordinates from the position tracking system 28 may not be perfectly aligned with those from high-resolution data (e.g., CT data) used in the 4D heart model because they are captured at different times. This means point set $P_i$ may not truly correspond to model Card. Thus, both the time correspondence as well as the space alignment preferably must be determined.

According to various embodiments, it may be assumed that for any point set $P_i$, the possible corresponding models are $C_{ixd}$ and its closest neighboring models such as Cixd±k, for example, if four neighbors are taken then k=[1, 2]. This assumption is valid because the timing difference of the magnetic tracked points and CT models are known not to be very large. All the candidate models for a point set $P_i$ may be written as $C_{ij}$ where j=[1, 5] if four neighbors are used and $C_{ixd}$ itself. A scheme S may be defined that selects one $C_{ij}$ as the corresponding model for each point set $P_i$.

The probability that is needed to maximize becomes p(F(P)|S, C), which is difficult to compute directly since S is not known. According to various embodiments, an EM algorithm can be used that can maximize this probability by maximizing the expected log likelihood log(p(F(P)|S, C)), assuming S is a hidden random variable.

To use the EM algorithm, the Q function, or the expected log likelihood, must be determined. If S is a random variable, then the expected log likelihood becomes:

$$Q(F(P), S, C) = \sum_S \log(p(F(P)|S, C)) f(S|C, F^{(k-1)}(P)), \quad (4)$$

log(p(F(P)|S, C)) is the log likelihood and $f(S|C, F^{(k-1)}(P))$ is the probability of a correspondence scheme S given the data C and alignment $F^{(k-1)}(P)$ found in the last iteration. It can be computed by:

$$f(S|C, F^{(k-1)}(P)) = \frac{p(F^{(k-1)}(P)|C, S)p(S|C)}{\sum_S p(F^{(k-1)}(P)|C, S)p(S|C)} \quad (5)$$

where $p(F^{(k-1)}(P)|C, S)$ is the probability of transformed points in the last iteration given model C, and the corresponding model for each point set $P_i$ is determined by S. p(S|C) is the prior probability of every correspondence scheme S. Next is to maximize the Q function.

In the E step, the probability $f(S|C, F^{(k-1)}(P))$ is computed for any S with the following formula:

$$f(S|C, F^{(k-1)}(P)) = \frac{1}{a} p(F^{(k-1)}(P)|C, S)p(S|C) \quad (6)$$

where a is the normalization term. The probability $p(F^{(k-1)}(P)|C, S)$ may be computed with the formula $\Pi_{i=}^m p(F_{(k-1)}(P_j)|C_{ij})$, where the corresponding $C_{ij}$ for $P_i$ is defined by S. $F^{(k-1)}$ is known, given the correspondence from S, $p(F^{(k-1)}(P)|C_{ij}$ can be computed with equation (3). Now each $f(S|C, F^{(k-1)}(P))$ is known and can be represented by f(S) in the M step.

In the M step, since the f(S) is known, which is the probability of any S given C and $F^{(k-1)}$, the Q function in equation (4) becomes $$Q = \sum_S \log(p(F(P)|S, C)) f(S). \quad (6b)$$

Then, to maximize the Q function is equivalent to maximizing the function below:

$$\operatorname*{argmax}_F \sum \log(p(F)(P)|C, S) f(S)) =$$

$$\operatorname*{argmax}_F \sum_S \log\left(\sum_{i=1}^m p(F)(P_i)|C_{ij}\right)_s f(S)\right) =$$

$$\operatorname*{argmax}_F \sum_S \left(\sum_{i=1}^m p(F)(P_i)|C_{ij}\right)_s f(S)\right) =$$

$$\operatorname*{argmax}_F \sum_S \sum_{i=1}^m \|F(P_i) - C_{ij}\| f(S)$$

where the corresponding model $C_{ij}$ is defined by S. Here it can be seen that the problem becomes to find a transformation function F to minimize a weighted distance function. For each scheme S, the distance function $\|F(P_i)-C_{ij}\|_s$ (in which the $C_{ij}$ is the corresponding model of $P_i$ defined by the particular S) is weighted by f(S) computed in E step. This minimization can be done by the modified ICP algorithm described above. The only difference is here that a weight is added when the points are combined together.

Then the $F^{(k-1)}$ may be replaced with the new F and process repeat. The EM algorithm may stop when transformation function F does not change more than a certain threshold or the alignment error is below a certain threshold. The initial values of F may be computed under the correspondence scheme in the ideal situation where Pi corresponds to $C_{ixd}$.

When "virtual touch" is used to collect surface registration points, the error distribution is different from when a physical touch is used, as in the prior art. Pixels extracted from different regions of the ultrasound image tend to have different error distributions and the registration algorithm should be modified accordingly. The following describes a detailed error model for "virtual touch" points.

Figure 6B:
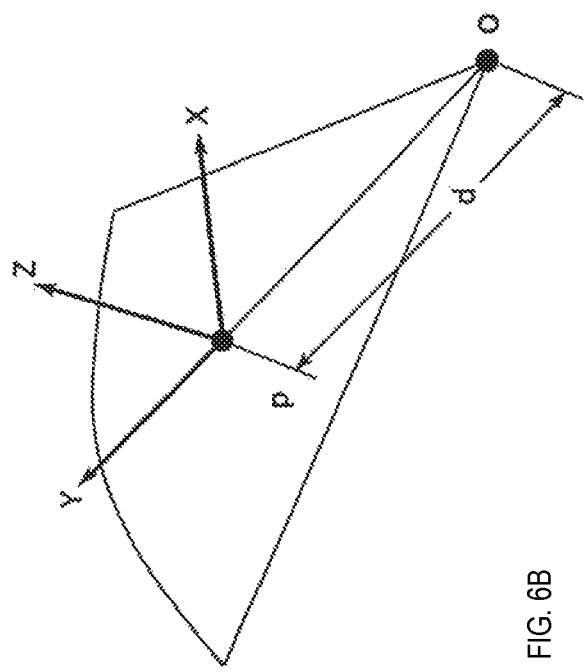
FIGS. 6A and 6B illustrate ultrasound distribution error.

Suppose one wants to know the error distribution of a pixel p that is d mm from the ultrasound image center O. To make the analysis easier, a local coordinate system may be used whose origin is at p, the X axis is on the image plane and perpendicular to the radius from O through p, the Y axis is the radius from image center O through p, and the Z axis is perpendicular to the image plane as shown in FIG. 6B.

Figure 6A:
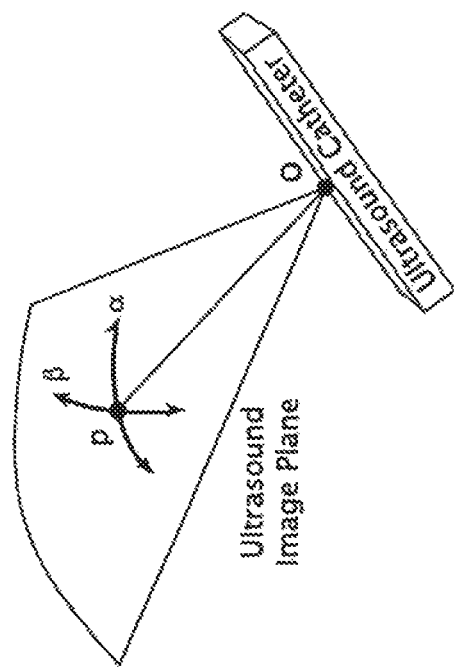

The image plane's angular error has two components as shown in FIG. 6A, one is the off plane angle β, and the other is the on plane angle α. All these angles are based on rotation pivot at the ultrasound image center O. These angles may be captured by the magnetic position sensor 24, which may have a few small coils inside it, which have known relative positions. Based on the position readings of these coils, the angles can be calculated. The position of the small coil may be assumed have an error of normal distribution $N(0, \Sigma_c)$ and the small coil has a distance $d_c$ to the image center. Then, when the 3D coordinate of a pixel is reconstructed which is d away from image center, it will have an error of normal distribution $$N\left(0, \frac{d}{d_c} \Sigma_c\right).$$

This means the error has been enlarged when the distance to the image center increases. Such error is only within the X-Z plane of the local coordinate system.

Ultrasound imaging devices calculate the echo energy of sound waves sent out from the image center to determine the surface's distance from the image center. Because the ultrasound image plane is not infinitely thin, when a plane with a thickness hits a surface, it will generate a band instead of a thin line in the ultrasound image. The thickness of the image plane increases proportionally to the distance from the image center. The error along the radius or Y-axis of the local coordinate system can be assumed to have a normal distribution of $N(0, d\sigma_d)$ where d is the distance of the pixel from image center.

Finally, the ultrasound image center O may have a normal error distribution. It will affect the 3D reconstruction of all the pixels in ultrasound image because all the coordinates are calculated relative to that of O. Combining all the errors together, in the local coordinate system of point p, the error can be modeled as a normal distribution with a mean of zero and a covariance matrix of:

$$\sum_d = d\sum_1 + \sum_O = d\begin{pmatrix} \sigma_{c_1} & 0 & 0 \\ 0 & \sigma_r & 0 \\ 0 & 0 & \sigma_{c_2} \end{pmatrix} + \begin{pmatrix} \sigma_{O_1} & 0 & 0 \\ 0 & \sigma_{O_2} & 0 \\ 0 & 0 & \sigma_{O_3} \end{pmatrix} \quad (7)$$

$\sigma_{c1}$, $\sigma_{c2}$, and $\sigma_{c3}$ are variance on the X, Y, and Z-axes of the local coordinate system of a pixel that is 1 mm away from the image center. For a pixel that is d mm from image center, the covariance matrix is d times $\Sigma_1$. $\Sigma_O$ is the position error of the image center O.

Assume a point $p(x, y, z)$ captured on an ultrasound image whose center is O and its normal is N. The local coordinate system's Y-axis will be $(p-O)/d$ where d is the distance from p to O. The Z-axis will be the plane normal N. The X-axis will be $(Y \times N)$. The origin of the local coordinate system will be p. Then, a transformation matrix M can be defined that transforms the global coordinate system into this local coordinate system and the error distribution's covariance matrix ρ for P can be written as:

$$\sum_p = M \sum_d M^T \quad (8)$$

The $\Sigma_d$ is defined in equation (7) above. In the local coordinate system, $\Sigma_d$ is a diagonal matrix, but in the global coordinate system, $\Sigma_p$ usually is not a diagonal matrix. The covariance matrix of the error distribution is dependent on p's position and the image plane's orientation from which p is extracted. So any surface registration point p will have a unique error distribution function $N(0, \Sigma_p)$.

The registration algorithm maximizes the probability of F(P) and C where P is the surface registration point set, F( ) is the current registration function, and C is the CT heart model. If the error distribution function is assumed to be a normal distribution, to maximize the probability equals to minimize the distance:

$$\operatorname*{argmax}_F \sum_{i=1}^m (F(p_i) - C_{pi}) \sum_{p_i}^{-1} (F(p_i) - C_{pi})^T \quad (9)$$

where m is the number of points in P, $p_i$ is the i'th point in point set P, $C_{pi}$ is the corresponding point of $p_i$ on heart model C. $\Sigma_{pi}$ is the covariance matrix for point $p_i$ as defined in equation (8). In equation (9), the distance is weighted by $\sum_{p_i}^{-1}$, so those points that have larger $\Sigma_{pi}$ (larger errors) will be weighted down accordingly. Points that are captured more accurately will have larger weight in the sum of distance. And since the $\Sigma_{pi}$ is not diagonal, the correlation of different axes has been considered as well.

Referring back to FIG. 3, at step 58, a local, free-form non-rigid registration may be performed to improve the accuracy of the registration at step 54. As mentioned previously, the catheter navigation system 10 can be used for left atrium ablation procedures. The left atrium is a highly motile and non-rigid object. Non-rigid shape changes result from multiple sources including: (1) the cardiac cycle or heart beat; (2) the breath cycle (i.e., the pressure changes of the lungs); and (3) other sources, like blood pressure, medicine and medical instruments. Preferably, a radial basis function is used to do the local non-rigid registration as described below.

Suppose the intra-operative surface registration point set is $P=(p_1, p_2, \ldots, p_n)$, and the heart model from CT is C. After global rigid registration, P and C still have difference $D=(d_1, d_2, \ldots, d)$. Here P is after the global registration. Each $d_i$ may be defined as $d_i = P_i - C_{pi}$, where $C_{pi}$ is the nearest point of $p_i$ in model C. The free-form non-rigid registration should find a transformation function $F_{local}(C)$ so that for any $i \in \{1, 2, \ldots, n\}$, $$p_i = F_{local}(C_{pi}) \quad (10)$$

which means that after this non-rigid local transformation $F_{local}$, all the surface registration points should be on the surface of the transformed model $F_{local}(C)$. Usually the $F_{local}(p)$ at any 3D position $p=(x, y, z)$ has the form of:

$$F_{local}(p) = p + \sum_{i=1}^n a_i \cdot \Phi(\|p - C_{p_i}\|) \quad (11)$$

where $\|*\|$ is the distance between two 3D points, $a_i$ is a 3D vector, also known as the coefficient for each point $C_{pi}$ and $\Phi( )$ is a radial basis function. For any point p, $F_{local}(p)$ add an offset to p. The offset is a weighted sum of all coefficients $a_i$ weighted by the radial basis function of the distance from p to $C_{pi}$. Also, $\|p - C_{pi}\|$ can be computed. With the constraint in equation (10), enough equations exist to solve each $a_i$:

$$p_i = C_{p_i} + \sum_{k=1}^n a_k \cdot \Phi(\|C_{p_i} - C_{p_k}\|) \quad (12)$$

A compactly supported positive definite radial basis function can be chose which ensures there is solution for equation (12):

$$\Phi(X) = \phi\left(\frac{\|X\|}{s}\right) \quad (13)$$

$$\phi(r) = (1-r)_+^4(3r^3 + 12r^2 + 16r + 4), r \geq 0 \quad (14)$$

where $(1-r)_+ = \max(1-r, 0)$, s is a pre-defined scale. For more information on compactly supported positive definite radial basis functions, see Z. Wu, "Multivariate compactly supported positive definite radial functions," AICM, volume 4, pages 283-292, 1995, which is incorporated by reference. This compactly supported radial basis ensures that each surface registration point only affects the non-rigid transformation locally. Also, it can reduce the computational cost. Moreover, equation (14) has been shown to have $C^2$ continuity. Therefore, the $F_{local}$ is $C^2$ continuous in the space and it satisfies the constraint shown in equation (11).

One example of this non-rigid local registration is shown in FIGS. 7A and 7B. Suppose that in a 3D model of a plane, there are several surface points that show the object is actually is curved. Rigid global registration cannot find a good alignment of the points and the model (see FIG. 7A). Using a radial basis local non-rigid registration, the model can be modified according to the surface points locally and non-rigidly. The result is a much better fit for the points (see FIG. 7B).

Figure 12:
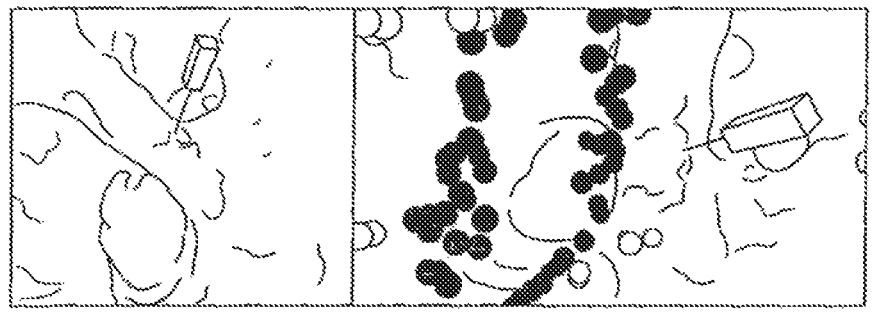
FIG. 12 shows an example of a real-time, high-resolution image output by the image-processing module of the catheter navigation system of FIG. 1 according to various embodiments of the present invention.

Once the registration is complete, as shown in FIG. 3, as the clinician moves the catheter 12 as part of a medical procedure (e.g., a left atrium ablation), at step 59, the image processing module 40 may output real-time, high resolution 3D models of the subject (e.g., the subject's heart) on the display unit 46, as shown in FIG. 12. The real-time high-resolution image may be generated based on data 60, including the ultrasound image data captured by the catheter 12, the position of the catheter 12 (as determined by the position tracking system 28), and on the timing signals (e.g., the ECG signals). The displayed real-time 3D heart module can aid the clinician in performing the procedure.

In various embodiments, the present invention can provide the following advantages. First, it can be more reliable than conventional catheter navigation systems. Because one does not need to touch physically the heart wall with the catheter but just to move the catheter inside the left atrium and take some pictures, there is no risk of pushing the heart wall too much nor the risk that a pixel is not actually on the heart wall.

Second, embodiments of the present invention can be faster than the prior art. When one takes one ultrasound image at one location with a catheter according to the present invention, one can capture tens or hundreds of points by virtual touch. This is much more efficient than previous methods. As a result, registration results could be more accurate. It is currently thought that the more registration points taken, the better the registration results. Because it is much faster and more reliable to capture registration points with a catheter according to embodiments of the present invention, one can capture tens or hundreds of times more points in the same amount of time using this technology than is possible with previous methods. This will result in better registration results.

Third, there may be a higher confidence of ablation sites. After registration, clinicians may navigate the catheter 12 based on the registration result. The 3D position of the ablation tip will be displayed with the heart model in real time. When a clinician moves the catheter near the site where the ablation should be performed, the ultrasound images from the heart wall can be visually verified. This adds confidence over merely measuring the distance from catheter tip position to the heart model's wall.

Various embodiments of the present invention are therefore directed to a method for producing images of a subject (e.g., a person's heart). The method may comprise the steps of (1) acquiring ultrasound images of the subject with a catheter comprising a position sensor; (2) capturing a plurality of 4D surface registration points in the acquired ultrasound images corresponding to points on the subject; and (3) registering a high resolution 4D model (e.g., a CT scan model) of the subject with the plurality of 4D surface registration points. The method may also comprise displaying high resolution, real-time images of the subject during a medical procedure based on the registration of the high resolution 4D model to the 4D surface registration points.

In another embodiment, the present invention is directed to a computer readable medium having stored thereon instructions, which when executed by a processor, cause the processor to: (1) capture a plurality of 4D surface registration points from a plurality of input ultrasound images corresponding to points on a subject's heart; and (2) register a high resolution 4D model (e.g., a CT scan model) of the subject's heart with the plurality of surface registration points. The computer readable medium may also comprise instructions that cause the processor to display high resolution, real-time images of the heart during a medical procedure on the subject based on the registration of the high resolution 4D model to the 4D surface registration point.

In yet another embodiment, the present invention is directed to a catheter navigation system that comprises: (1) a catheter comprising an ultrasound transducer and a magnetic position sensor; (2) a position tracking system for tracking the position of the catheter based on signals received by the magnetic position sensor; (3) an image processing module in communication with the catheter and the position tracking system for: (i) capturing a plurality of 4D surface registration points from a plurality of ultrasound images of one or more inner heart walls of a subject's heart acquired by the catheter; and (ii) registering a high resolution 4D model of the subject's heart with the plurality of 4D surface registration points. The system may also comprise a display in communication with the image-processing module for displaying high-resolution images of the heart during a medical procedure on the subject based on the registration of the high resolution 4D model to the 4D surface registration points.

In yet another embodiment, the present invention is directed to a method of performing a medical procedure on a subject (e.g., a heart of a human being). The method may comprise: (1) inserting, by a clinician (e.g., a surgeon), a first catheter into the subject (e.g., the subject's heart); (2) acquiring ultrasound images of the subject with the first catheter; (3) capturing, with a programmed computer device in communication with the catheter, a plurality of 4D surface registration points in the acquired ultrasound images corresponding to points on the subject (e.g., inner heart walls of the subject); (4) registering, with the programmed computer device, a high resolution 4D model of the subject with the plurality of surface registration points; and (5) displaying, on a display in communication with the computing device, high resolution, real-time images of the subject (e.g., the subject's heart) during the medical procedure based on the registration of the high resolution 4D model to the 4D surface registration points. In various implementations, the first catheter may comprise an interventional device. In other implementations, the clinician may insert a second catheter that comprises an interventional device into the subject.

While several embodiments of the present invention have been described herein, it should be apparent that various modifications, alterations, and adaptations to those embodiments may occur to persons skilled in the art. It is therefore intended to cover all such modifications, alterations, and adaptations without departing from the scope and spirit of the present invention as defined by the appended claims.

What is claimed is:

1. A computer-implemented method, comprising:
receiving an ultrasound image of a heart, the ultrasound image being acquired from within the heart by a catheter comprising a position sensor;
capturing a plurality of four-dimensional (4D) surface registration points corresponding to points on the heart based on the ultrasound image of the heart and position data acquired by the position sensor associated with the position of the catheter when the ultrasound image was acquired by the catheter; and
registering, in space and time, a high resolution 4D model of the heart with the plurality of 4D surface registration points; wherein the model is separate from the ultrasound image.

2. The computer-implemented method of claim 1, wherein the position data acquired by the position sensor associated with the position of the catheter includes data regarding an orientation of the catheter.

3. The computer-implemented method of claim 1, further comprising capturing the plurality of 4D surface registration points based on data associated with a phase of a cardiac cycle when the ultrasound image was acquired.

4. The computer-implemented method of claim 3, further comprising synchronizing the high resolution 4D model with the data associated with the phase of the cardiac cycle via an electrocardiogram.

5. The computer-implemented method of claim 1, further comprising capturing the plurality of 4D surface registration points corresponding to points on the heart without the catheter touching any of the points on the heart.

6. The computer-implemented method of claim 1, further comprising constructing the high-resolution 4D model of the heart from a series of three-dimensional (3D) models at successive time points.

7. The computer-implemented method of claim 1, further comprising generating the series of 3D models prior to acquiring the ultrasound image.

8. The computer-implemented method of claim 6, further comprising generating the series of 3D models after acquiring the ultrasound image.

9. A catheter navigation system comprising:
a catheter comprising an ultrasound transducer and a magnetic position sensor, the ultrasound transducer being configured to collect data for generation of an ultrasound image of a portion of a heart;
a position tracking system configured to track the position of the catheter based on signals received by the magnetic position sensor;
an image processor in communication with the catheter and the position tracking system configured to:
capture a plurality of four-dimensional (4D) surface registration points in the ultrasound image corresponding to points on the heart based on the ultrasound image of the heart and position data acquired by the position sensor associated with the position of the catheter when the ultrasound image was acquired by the catheter; and
registering, in space and time, a high resolution 4D model of the heart with the plurality of 4D surface registration points; wherein the model is separate from the ultrasound image.

10. The catheter navigation system of claim 9, wherein the high resolution 4D model of the heart is constructed from a series of three-dimensional (3D) models at successive time points.

11. The catheter navigation system of claim 10, wherein the series of 3D models comprises a series of 3D CT scans taken at successive time points.

12. The catheter navigation system of claim 9, wherein the image processor registers the plurality of 4D surface registration points by determining a transformation function that aligns the 4D surface registration points to the 4D model.

13. The catheter navigation system of claim 12, wherein the image processor determines the transformation function by iteratively determining the transformation function until the transformation function does not change more than a particular threshold.

14. The catheter navigation system of claim 12, wherein the image processor determines the transformation function by iteratively determining the transformation function until an alignment error is below a particular threshold.

15. A catheter navigation system comprising:
a catheter, comprising:
an elongate shaft including a proximal portion and a distal portion;
an ablation device disposed on the distal portion of the elongate shaft configured to deliver ablation energy to tissue;
a position sensor; and
an ultrasound transducer disposed on the distal portion of the elongate shaft, wherein the ultrasound transducer is configured to transmit ultrasound and for receiving resultant echoes from the tissue;
a position tracking system configured to track a position of the catheter based on signals received by the position sensor; and
an image processor configured to:
capture a plurality of four-dimensional (4D) surface registration points in an ultrasound image corresponding to points on a heart based on the ultrasound image of the heart and position data acquired by the position sensor associated with the position of the catheter when the ultrasound image was acquired by the catheter; and
register, in space and time, a high resolution 4D model of the heart with the plurality of 4D surface registration points, wherein the model is separate from the ultrasound image.

16. The catheter navigation system of claim 15, wherein the position sensor comprises a magnetic positioning system.

17. The catheter navigation system of claim 16, wherein the image processor is configured to be in communication with the ablation catheter and the position tracking system.

18. The catheter navigation system of claim 17, wherein the image processor is configured to generate real-time three-dimensional images of the tissue from ultrasound image data generated from the resultant echoes.

19. The medical device of claim 16, wherein the ablation device is disposed distally with respect to the ultrasound transducer.

* * * * *